US011207435B2

(12) United States Patent
Dobrinsky

(10) Patent No.: US 11,207,435 B2
(45) Date of Patent: Dec. 28, 2021

(54) HUMIDIFIER DISINFECTION USING ULTRAVIOLET LIGHT

(71) Applicant: Sensor Electronic Technology, Inc., Columbia, SC (US)

(72) Inventor: Alexander Dobrinsky, Silver Spring, MD (US)

(73) Assignee: Sensor Electronic Technology, Inc., Columbia, SC (US)

( * ) Notice: Subject to any disclaimer, the term of this patent is extended or adjusted under 35 U.S.C. 154(b) by 91 days.

(21) Appl. No.: 16/261,711

(22) Filed: Jan. 30, 2019

(65) Prior Publication Data

US 2019/0231912 A1  Aug. 1, 2019

Related U.S. Application Data

(60) Provisional application No. 62/624,741, filed on Jan. 31, 2018.

(51) Int. Cl.
*A61L 2/10* (2006.01)
*A61M 16/16* (2006.01)
*A61L 2/24* (2006.01)

(52) U.S. Cl.
CPC ............................ *A61L 2/10* (2013.01); *A61L 2/24* (2013.01); *A61M 16/161* (2014.02); *A61L 2202/11* (2013.01); *A61M 2205/3306* (2013.01)

(58) Field of Classification Search
CPC . A61L 2/10; A61L 2/24; A61M 16/16; A61M 16/161; F24F 6/00
See application file for complete search history.

(56) References Cited

U.S. PATENT DOCUMENTS

| | | | |
|---|---|---|---|
| 7,553,456 B2 | 6/2009 | Gaska et al. |
| 7,634,996 B2 | 12/2009 | Gaska et al. |
| 8,277,734 B2 | 10/2012 | Koudymov et al. |
| 8,980,178 B2 | 3/2015 | Gaska et al. |
| 9,006,680 B2 | 4/2015 | Bettles et al. |
| 9,034,271 B2 | 5/2015 | Shur et al. |
| 9,061,082 B2 | 6/2015 | Gaska et al. |
| 9,138,499 B2 | 9/2015 | Bettles et al. |
| 9,179,703 B2 | 11/2015 | Shur et al. |

(Continued)

FOREIGN PATENT DOCUMENTS

WO  WO-2013147623 A1 * 10/2013 .......... A61M 16/167

*Primary Examiner* — Walter D. Griffin
*Assistant Examiner* — Cameron J Allen
(74) *Attorney, Agent, or Firm* — LaBatt, LLC

(57) ABSTRACT

Aspects of the invention provide a system for disinfecting a humidifier containing a volume of water. An enclosure, such as a humidifier, includes a first chamber, a second chamber, a humidifier component, a third chamber, and a control unit. The first chamber contains a volume of water and a portion of the water flows into the second chamber. A first set of ultraviolet radiation sources within the first chamber can be configured to generate UV-A radiation, while a second set of ultraviolet radiation sources within the second chamber can be configured to generate UV-C radiation. In operation, the humidifier component adjacent to the second chamber creates water vapor using the portion of the volume of water within the second chamber. The water vapor flows into a third chamber that contains the water vapor and releases the water vapor into the ambient.

20 Claims, 5 Drawing Sheets

(56) References Cited

U.S. PATENT DOCUMENTS

| | | |
|---|---|---|
| 9,482,440 B2 | 11/2016 | Markham et al. |
| 9,572,903 B2 | 2/2017 | Dobrinsky et al. |
| 9,603,960 B2 | 3/2017 | Dobrinsky et al. |
| 9,687,577 B2 | 6/2017 | Dobrinsky et al. |
| 9,707,307 B2 | 7/2017 | Shur et al. |
| 9,718,706 B2 | 8/2017 | Smetona et al. |
| 9,724,441 B2 | 8/2017 | Shur et al. |
| 9,732,969 B2 | 8/2017 | Lee et al. |
| 9,750,830 B2 | 9/2017 | Shur et al. |
| 9,757,486 B2 | 9/2017 | Dobrinsky et al. |
| 9,795,699 B2 | 10/2017 | Shur et al. |
| 9,801,965 B2 | 10/2017 | Bettles et al. |
| 9,802,840 B2 | 10/2017 | Shturm et al. |
| 9,878,061 B2 | 1/2018 | Shur et al. |
| 9,919,068 B2 | 3/2018 | Shur et al. |
| 9,974,877 B2 | 5/2018 | Bettles et al. |
| 9,981,051 B2 | 5/2018 | Shur et al. |
| 9,987,383 B2 | 6/2018 | Bilenko et al. |
| 9,999,782 B2 | 6/2018 | Shur et al. |
| 10,004,821 B2 | 6/2018 | Dobrinsky et al. |
| 10,040,699 B2 | 8/2018 | Smetona et al. |
| 10,099,944 B2 | 10/2018 | Smetona et al. |
| 2013/0048545 A1 | 2/2013 | Shatalov et al. |
| 2013/0175711 A1 | 7/2013 | Nutter et al. |
| 2014/0202962 A1 | 7/2014 | Bilenko et al. |
| 2015/0297877 A1* | 10/2015 | Pelkus .................. A61M 39/24 128/203.12 |
| 2016/0114186 A1 | 4/2016 | Dobrinsky et al. |
| 2017/0057842 A1 | 3/2017 | Dobrinsky et al. |
| 2017/0100495 A1 | 4/2017 | Shur et al. |
| 2017/0189711 A1 | 7/2017 | Shur et al. |
| 2017/0245527 A1 | 8/2017 | Dobrinsky et al. |
| 2017/0245616 A1 | 8/2017 | Lakios et al. |
| 2017/0281812 A1 | 10/2017 | Dobrinsky et al. |
| 2017/0290934 A1 | 10/2017 | Dobrinsky et al. |
| 2017/0368215 A1 | 12/2017 | Shatalov et al. |
| 2018/0028700 A1 | 2/2018 | Dobrinsky et al. |
| 2018/0092308 A1 | 4/2018 | Dobrinsky et al. |
| 2018/0104368 A1 | 4/2018 | Dobrinsky et al. |
| 2018/0117194 A1 | 5/2018 | Dobrinsky et al. |
| 2018/0185529 A1 | 7/2018 | Shur et al. |
| 2018/0221521 A1 | 8/2018 | Shur et al. |
| 2018/0243458 A1 | 8/2018 | Shatalov et al. |
| 2018/0339075 A1 | 11/2018 | Kennedy et al. |
| 2019/0030477 A1 | 1/2019 | Shatalov |
| 2019/0098842 A1 | 4/2019 | Barber, III et al. |
| 2019/0099613 A1 | 4/2019 | Estes et al. |
| 2019/0100445 A1 | 4/2019 | Dobrinsky |
| 2019/0100718 A1 | 4/2019 | Estes et al. |
| 2019/0117811 A1 | 4/2019 | Barber, III |
| 2019/0125907 A1 | 5/2019 | Dobrinsky |
| 2019/0135659 A1 | 5/2019 | Smetona et al. |
| 2019/0201570 A1 | 7/2019 | Dobrinsky et al. |

\* cited by examiner

HUMIDIFIER DISINFECTION USING ULTRAVIOLET LIGHT

REFERENCE TO RELATED APPLICATIONS

The current application claims the benefit of U.S. Provisional Application No. 62/624,741, filed on 31 Jan. 2018, which is hereby incorporated by reference.

TECHNICAL FIELD

The disclosure relates generally to disinfection with ultraviolet light, and more particularly, to disinfecting water and/or surfaces within a humidifier using ultraviolet light.

BACKGROUND ART

Water treatment using ultraviolet (UV) radiation offers many advantages over other forms of water treatment, such as chemical treatment. For example, treatment with UV radiation does not introduce additional chemical or biological contaminants into the water. Furthermore, ultraviolet radiation provides one of the most efficient approaches to water decontamination since there are no microorganisms known to be resistant to ultraviolet radiation, unlike other decontamination methods, such as chlorination. UV radiation is known to be highly effective against bacteria, viruses, algae, molds and yeasts. For example, hepatitis virus has been shown to survive for considerable periods of time in the presence of chlorine, but is readily eliminated by UV radiation treatment. The removal efficiency of UV radiation for most microbiological contaminants, such as bacteria and viruses, generally exceeds 99%. To this extent, UV radiation is highly efficient at eliminating *E-coli, Salmonella,* Typhoid fever, Cholera, Tuberculosis, Influenza Virus, Polio Virus, and Hepatitis A Virus.

Intensity, radiation wavelength, and duration of radiation are important parameters in determining the disinfection rate of UV radiation treatment. These parameters can vary based on a particular target culture. The UV radiation does not allow microorganisms to develop an immune response, unlike the case with chemical treatment. The UV radiation affects biological agents by fusing and damaging the DNA of microorganisms, and preventing their replication. Also, if a sufficient amount of a protein is damaged in a cell of a microorganism, the cell enters apoptosis or programmed death. FIG. 1 shows an illustrative germicidal effectiveness curve of ultraviolet radiation according to the prior art. As illustrated, the most lethal radiation is at wavelengths of approximately 260-270 nanometers.

Ultraviolet radiation disinfection using mercury-based lamps is a well-established technology. In general, a system for treating water using ultraviolet radiation is relatively easy to install and maintain in a plumbing or septic system. Use of UV radiation in such systems does not affect the overall system. However, it is often desirable to combine an ultraviolet purification system with another form of filtration since the UV radiation cannot neutralize chlorine, heavy metals, and other chemical contaminants that may be present in the water. Various membrane filters for sediment filtration, granular activated carbon filtering, reverse osmosis, and/or the like, can be used as a filtering device to reduce the presence of chemicals and other inorganic contaminants.

Mercury lamp-based ultraviolet radiation disinfection has several shortcomings when compared to deep ultraviolet (DUV) light emitting device (LED)-based technology, particularly with respect to certain disinfection applications. For example, in rural and/or off-grid locations, it is desirable for an ultraviolet purification system to have one or more of various attributes such as: a long operating lifetime, containing no hazardous components, not readily susceptible to damage, requiring minimal operational skills, not requiring special disposal procedures, capable of operating on local intermittent electrical power, and/or the like. The use of a DUV LED-based solution can provide a solution that improves one or more of these attributes as compared to a mercury vapor lamp-based approach. For example, in comparison to mercury vapor lamps, DUV LEDs: have substantially longer operating lifetimes (e.g., by a factor of ten); do not include hazardous components (e.g., no mercury), which require special disposal and maintenance; are more durable in transit and handling (e.g., no filaments or glass); have a faster startup time; have a lower operational voltage; are less sensitive to power supply intermittency; are more compact and portable; can be used in moving devices; can be powered by photovoltaic (PV) technology, which can be installed in rural locations having no continuous access to electricity and having scarce resources of clean water; and/or the like.

SUMMARY OF THE INVENTION

Aspects of the invention provide a system for disinfecting a humidifier containing a volume of water. In an embodiment, an enclosure, such as a humidifier, includes a first chamber, a second chamber, a humidifier component, a third chamber, and a control unit. The first chamber contains a volume of water and a portion of the water flows into the second chamber. A first set of ultraviolet radiation sources within the first chamber is configured to generate UV-A radiation, while a second set of ultraviolet radiation sources within the second chamber is configured to generate UV-C radiation. In operation, the humidifier component adjacent to the second chamber vaporizes the portion of the volume of water within the second chamber into water vapor. The water vapor flows into a third chamber that contains the water vapor and releases the water vapor into the ambient.

A first aspect of the invention provides an enclosure comprising: a first chamber containing a volume of water, the first chamber including a first set of ultraviolet radiation sources configured to generate ultraviolet radiation in a UV-A wavelength range; a second chamber fluidly connected to the first chamber, the second chamber including a second set of ultraviolet radiation sources configured to generate ultraviolet radiation in a UV-C wavelength range, wherein a portion of the volume of water flows into the second chamber; a humidifier component adjacent to the second chamber configured to create water vapor from the portion of the volume of water within the second chamber; a third chamber connected to the humidifier component, the third chamber configured to contain the water vapor and release the water vapor into ambient; and a control unit configured to monitor a set of current conditions for the first chamber and the second chamber and adjust operation of the first set of ultraviolet radiation sources and the second set of ultraviolet radiation sources based on the set of current conditions.

A second aspect of the invention provides a system comprising: a humidifier comprising: a first chamber containing a volume of water, the first chamber including a first set of ultraviolet radiation sources configured to generate ultraviolet radiation in a UV-A wavelength range; a second chamber fluidly connected to the first chamber, the second chamber including a second set of ultraviolet radiation sources configured to generate ultraviolet radiation in a UV-C wavelength range, wherein a portion of the volume of water flows into the second chamber; a humidifier component adjacent to the second chamber configured to create water vapor from the portion of the volume of water within the second chamber; and a third chamber connected to the humidifier component, the third chamber configured to contain the water vapor and release the water vapor into ambient; and a control unit configured to monitor a set of current conditions for the first chamber and the second chamber, the set of current conditions including a transparency of the water to UV-A and UV-C radiation, and adjust operation of the first set of ultraviolet radiation sources and the second set of ultraviolet radiation sources based on the set of current conditions.

A third aspect of the invention provides a system comprising: a humidifier comprising: a first chamber containing a volume of water, the first chamber including a first set of ultraviolet radiation sources configured to generate ultraviolet radiation in a UV-A wavelength range; a second chamber fluidly connected to the first chamber, the second chamber including a second set of ultraviolet radiation sources configured to generate ultraviolet radiation in a UV-C wavelength range, wherein a portion of the volume of water flows into the second chamber; a humidifier component adjacent to the second chamber configured to create water vapor from the portion of the volume of water within the second chamber; and a third chamber connected to the humidifier component, the third chamber including a third set of ultraviolet radiation sources configured to generate ultraviolet radiation in the UV-C wavelength range, wherein the third chamber is configured to contain the water vapor and release the water vapor into ambient; and a control unit configured to monitor a set of current conditions for the first chamber, the second chamber, and the third chamber, the set of current conditions including a humidity level within the third chamber, and adjust operation of the first set of ultraviolet radiation sources, the second set of ultraviolet radiation sources, and the third set of ultraviolet radiation sources based on the set of current conditions.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a system for disinfecting a humidifier containing a volume of water. In an embodiment, an enclosure, such as a humidifier, includes a first chamber, a second chamber, a humidifier component, a third chamber, and a control unit. The first chamber contains a volume of water and a portion of the water flows into the second chamber. A first set of ultraviolet radiation sources within the first chamber is configured to generate UV-A radiation, while a second set of ultraviolet radiation sources within the second chamber is configured to generate UV-C radiation. In operation, the humidifier component adjacent to the second chamber vaporizes the portion of the volume of water within the second chamber into water vapor. The water vapor flows into a third chamber that contains the water vapor and releases the water vapor into the ambient.

As used herein, unless otherwise noted, the term "approximately" is inclusive of values within +/− ten percent of the stated value. Unless otherwise stated, two values are "similar" when the smaller value is within +/− twenty-five percent of the larger value.

Furthermore, as used herein, ultraviolet radiation/light means electromagnetic radiation having a wavelength ranging from approximately 10 nanometers (nm) to approximately 400 nm, while ultraviolet-C (UV-C) means electromagnetic radiation having a wavelength ranging from approximately 100 nm to approximately 280 nm, ultraviolet-B (UV-B) means electromagnetic radiation having a wavelength ranging from approximately 280 to approximately 315 nanometers, and ultraviolet-A (UV-A) means electromagnetic radiation having a wavelength ranging from approximately 315 to approximately 400 nanometers.

As also used herein, a layer is a transparent layer when the layer allows at least ten percent of radiation having a target wavelength, which is radiated at a normal incidence to an interface of the layer, to pass there through. Furthermore, as used herein, a layer is a reflective layer when the layer reflects at least ten percent of radiation having a target wavelength, which is radiated at a normal incidence to an interface of the layer.

Figure 1:
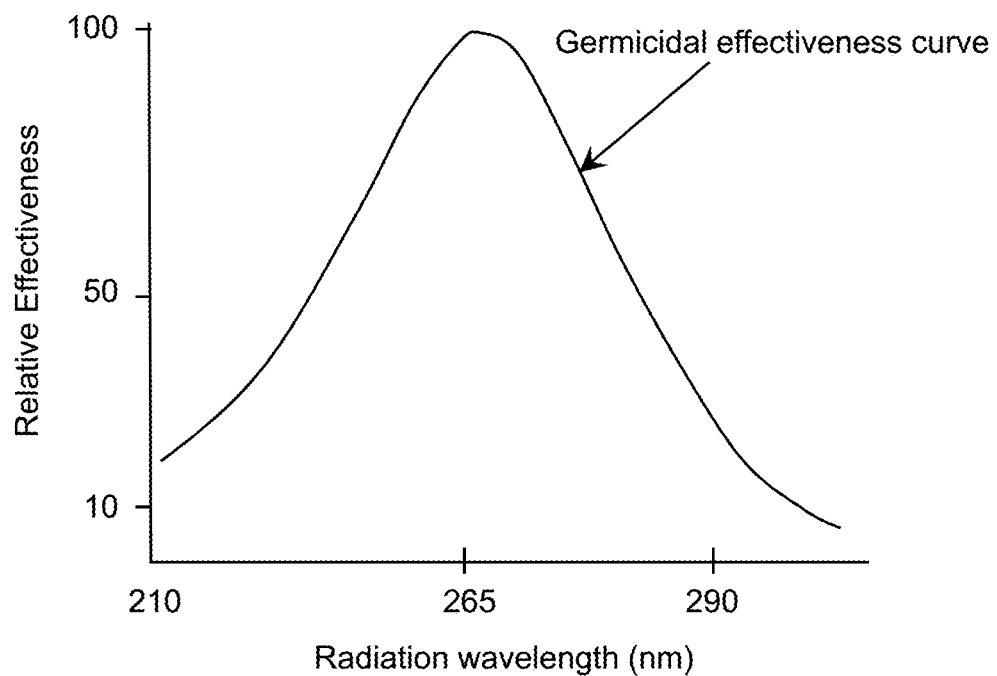
FIG. 1 shows an illustrative germicidal effectiveness curve of ultraviolet radiation according to the prior art.
Figure 2:
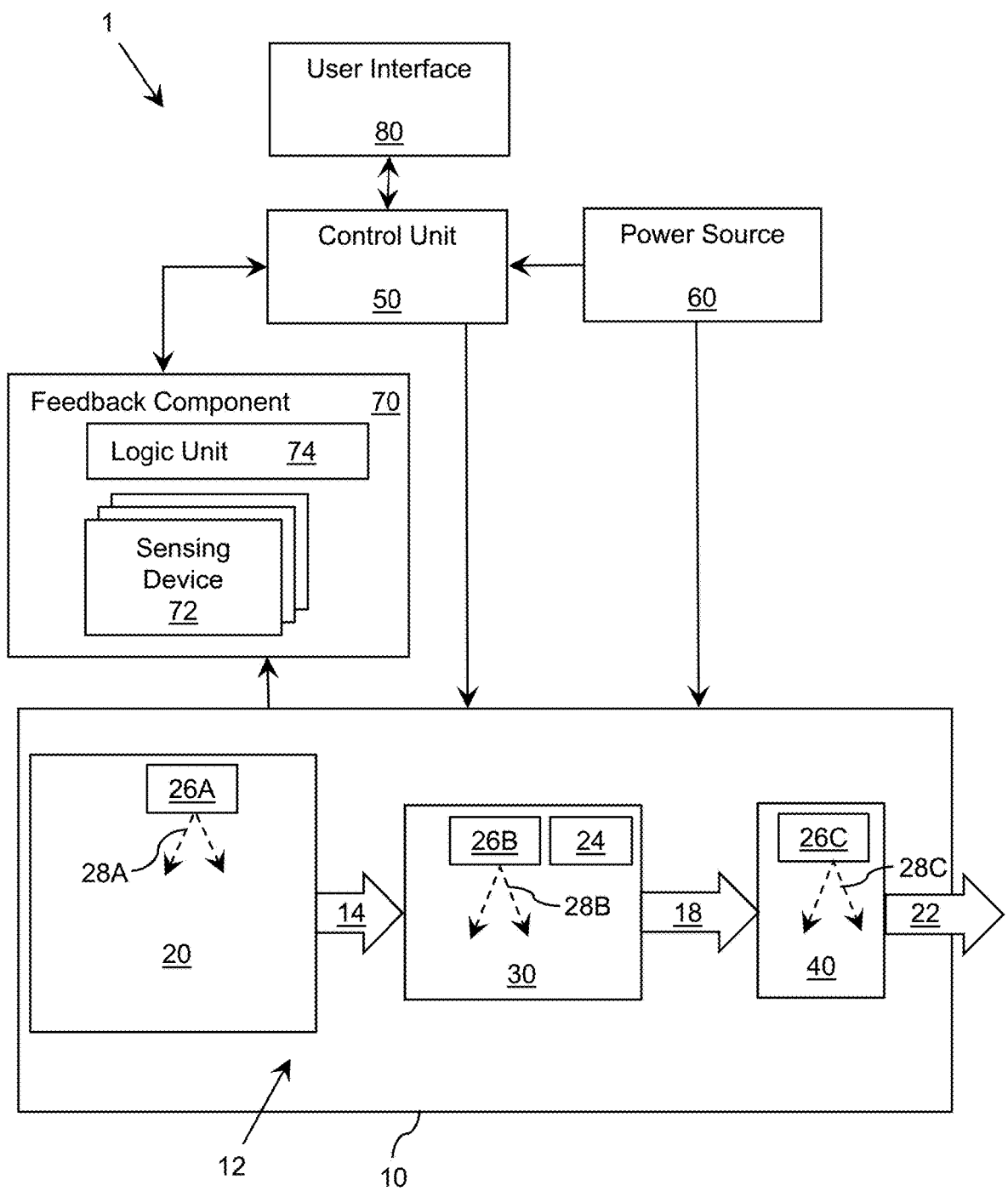
FIG. 2 shows an illustrative system for disinfecting a humidifier according to an embodiment.

Turning to the drawings, FIG. 2 shows an illustrative system 1 for sterilizing a liquid (e.g., water) in an enclosure 10 according to an embodiment. The liquid in the enclosure 10 can be used to introduce humidity into an ambient in order to increase the moisture content the ambient. An example of such an enclosure 10 is a humidifier. The enclosure 10 can include a fluid flow path 12. The fluid flow path 12 includes a first chamber 20, a second chamber 30, and a third chamber 40. The first chamber 20, the second chamber 30, and the third chamber 40 can be fluidly connected 14, 18 by any means. For example, the first chamber 20 and the second chamber 30 can be connected by a tube or a channel with the flow of fluid there through being controlled by a valve. In an embodiment, a water filter (not shown) can be located between the first chamber 20 and the second chamber 30. In another example, the first chamber 20 and the second chamber 30 can each include an opening and the openings of each chamber 20, 30 can be aligned in order for a portion of the water within the first chamber 20 to flow to the second chamber 30. One or both openings can include any mechanism, such as a valve, to open and close the opening(s) in order to allow and stop the water from flowing. Regardless, it is understood that the water in the first chamber 20 can flow into the second chamber 30. In an embodiment, the water is dispensed into the first chamber 20 and stored in the second chamber 30 for a time/duration that is shorter than a time/duration that the water is stored in the first chamber 20.

The second chamber 30 and the third chamber 40 are also fluidly connected 18 using any solution (e.g., a tube, a channel, valve(s), and/or the like). The second chamber 30 can include a humidifier component 24 that vaporizes at least a portion of the liquid within the second chamber 30. The vapor can flow through the connection 18 into the third chamber 40 (e.g., a vapor chamber 40). The third chamber 40 includes an exit path 22 for the vapor to flow out of the enclosure 10 and into the ambient in order to introduce humidity into the ambient.

Although it is not shown, it is understood that the first chamber 20 includes an inlet configured for receiving the liquid. The inlet can be selectively opened and closed using any solution, such as a removable cap. Also, although it is not shown, a filter can be located at the inlet in order to filter the water before entering the first chamber 20. In an embodiment, the first chamber 20 is sized to store a minimum amount of water that is required to treat a particular size room throughout the night (e.g., approximately 8 hours). For example, the first chamber 20 can be sized to contain approximately a gallon of water. However, it is understood that the first chamber 20 can be any size that is larger than the size of the second chamber 30. Additionally, the second chamber 30 can be larger than the third chamber 40. In another embodiment, the first chamber 20 can be connected to a water source, which can be configured to automatically refill the first chamber 20 to a predetermined maximum in response to the amount of water in the first chamber 20 being lower than a predetermined minimum.

The humidifier component 24 can be located within the second chamber 30 or between the second chamber 30 and the third chamber 40. In an embodiment, the humidifier component 24 can be an ultrasonic nebulizer that includes a metal diaphragm that vibrates at an ultrasonic frequency to create vapor droplets. In another embodiment, the humidifier component 24 can be an evaporative humidifier (e.g., a wick/filter) that absorbs water from the second chamber 30 and a fan blown over the evaporative humidifier can release the vapor. Other embodiments for the humidifier component 24 can include a steam humidifier that heats or boils the water to form the vapor, an impeller that uses a rotating disc to fling water at a diffuser that breaks up the water into fine water droplets, and/or the like.

The first chamber 20, the second chamber 30, and the third chamber 40 can each include a set of ultraviolet radiation sources 26A-26C, respectively. Examples of an ultraviolet radiation source included in each set of ultraviolet radiation sources 26A-26C include, but are not limited to, one or more of: an ultraviolet light emitting diode (LED), a super luminescent LED, a laser diode, and/or the like. In one embodiment, the ultraviolet light source can comprise an LED manufactured with one or more layers of materials selected from the group-III nitride material system (e.g., $Al_xIn_yGa_{1-x-y}N$, where $0 \leq x, y \leq 1$, and $x+y \leq 1$ and/or alloys thereof).

Any combination of one or more solutions for mounting the sets of ultraviolet radiation sources 26A-26C within the chambers 20, 30, 40 can be used. For example, the sets of ultraviolet radiation sources 26A-26C can be embedded within the walls of the chambers 20, 30, 40. Alternatively, a set of ultraviolet radiation sources 26A-26C can be adhered to a surface within the chambers 20, 30, 40.

Additionally, the sets of ultraviolet radiation sources 26A-26C can each comprise one or more additional components (e.g., a wave guiding structure, a component for relocating and/or redirecting an ultraviolet radiation source, etc.) to direct and/or deliver the emitted radiation to a particular location/area, in a particular direction, in a particular pattern, and/or the like. Illustrative wave guiding structures include, but are not limited to: a wave guide; a plurality of ultraviolet fibers, each of which terminates at an opening; a diffuser; and/or the like. In an embodiment, one or more of the sets of ultraviolet radiation sources 26A-26C can comprise a lens manufactured from an ultraviolet transparent material, which is designed to direct the ultraviolet radiation to one or more locations within the chamber 20, 30, 40. In an embodiment, a set of ultraviolet radiation sources 26A-26C can comprise a reflective parabolic mirror designed to collimate the ultraviolet radiation. However, it is understood that these components are only illustrative of various possible components. To this extent, it is understood that other optical elements such as prisms, ultraviolet transparent windows, etc., can be employed.

Each of the sets of ultraviolet radiation sources 26A-26C can be configured to emit any type of ultraviolet radiation (e.g., radiation having a peak wavelength in a range of 10 nanometers to 400 nanometers) suitable for performing a desired disinfection. For example, the ultraviolet radiation emitted by a set of ultraviolet radiation sources 26A-26C can have a peak wavelength selected to damage the DNA structure of any bacteria that may be present in the water or vapor within the corresponding chamber 20, 30, 40.

In an embodiment, the set of ultraviolet radiation sources 26A for the first chamber 20 can generate ultraviolet radiation 28A in the UV-A range and/or high visible light range. For example, the set of ultraviolet radiation sources 26A can operate to emit radiation 28A with predominant wavelength(s) in the wavelength range of approximately 330 nanometers (nm) to approximately 420 nm. In an embodiment, the set of ultraviolet radiation sources 26B for the second chamber 30 can generate ultraviolet radiation 28B in the UV-C range. For example, the set of ultraviolet radiation sources 26B can operate to emit radiation 28B with predominant wavelength(s) in the wavelength range of approximately 260 nm to approximately 290 nm.

In an embodiment, the time/duration of the exposure of the UV-A ultraviolet radiation within the first chamber 20 is longer than the time/duration of the exposure of the UV-C ultraviolet radiation within the second chamber 30. For example, the time/duration of the UV-A exposure can range from ten minutes to tens of hours, while the time/duration of the UV-C exposure can be five minutes or less. In an embodiment, the UV-A radiation in the first chamber 20 is operated continuously when power is available to the enclosure 10 and a liquid is located within the first chamber 20, while the UV-C radiation in the second chamber 30 is only turned on when the enclosure (humidifier) 10 is turned on (e.g., the humidifier component 24 is vaporizing the water within the second chamber 30).

In an embodiment, the first chamber 20 can be an enclosure with a set of walls. As described herein, the set of ultraviolet radiation sources 26A can be embedded within or adhered to a surface of at least one of the walls in the set of walls. For example, the set of ultraviolet radiation sources 26A can be located on a top surface of the first chamber 20. In an embodiment, the set of ultraviolet radiation sources 26A can be located and oriented to allow irradiation of the water within the first chamber 20 even if the first chamber 20 is not filled to capacity.

As described herein, the set of ultraviolet radiation sources 26A can emit ultraviolet radiation 28A in the UV-A wavelength range. In an embodiment, a set of optical elements can be located adjacent to the set of ultraviolet radiation sources 26A in order to dissipate and distribute the UV-A radiation 28A throughout the first chamber 20. For example, the set of optical elements can comprise UV transparent diffusive structures, UV reflective diffusive structures, optical waveguiding elements, and/or the like. In an embodiment, the optical waveguiding elements can comprise glass, silicon dioxide ($SiO_2$), transparent polymers, transparent oxides, such as $Al_2O_3$, $CaF_2$, $MgF_2$, and/or the like.

In an embodiment, one or more interior surfaces of the first chamber 20 is capable of reflecting the ultraviolet radiation in order to recycle the ultraviolet radiation within the first chamber 20. In a more specific embodiment, at least the surface located opposite the set of ultraviolet radiation sources 26A includes a reflective surface. The reflective surface can include regions that are specularly reflective, diffusively reflective, and/or both. In an embodiment, such a reflective surface or regions of the reflective surface can comprise polished aluminum, a fluoropolymer, such as ethylene fluorinated ethylene-propylene (EFEP), expanding polytetrafluoroethylene (ePTFE) membrane (e.g., GORE® DRP® Diffuse Reflector Material), polytetrafluoroethylene (PTFE, e.g., Teflon®), and/or the like. The reflective regions can also comprise a dielectric or plastic material. For example, the reflective regions can comprise glass mirrors (e.g., a glass with evaporated metal), plastics, and/or the like.

In an embodiment, the first chamber 20 can include components and/or configurations that cause active or passive mixing of the water within the chamber 20. For example, the inlet (not shown) for the first chamber 20 can be located at the top of the enclosure so that when water enters the first chamber 20, gravity aids in mixing the water. Examples of mixing components can include, but are not limited to, stirrers with paddles, fluid circulation pumps, flow barriers, etc.

In an embodiment, at least a portion of the set of walls for the first chamber 20 can also include a photocatalyst. Ultraviolet radiation in the UV-A range can increase the presence of reactive oxygen species (ROS) within the water, which can contribute to the decay of the microorganisms. In an embodiment, the set of ultraviolet radiation sources 26A that emit UV-A radiation 28A can be combined with a photocatalyst located on at least a portion of the set of walls of the first chamber 20 to increase hydroxyl group radicals and/or ROS within the water to suppress microorganism growth. The photocatalyst can comprise any suitable photocatalyst, such as for example, $TiO_2$, copper, silver, copper/silver particles, platinum/palladium particles, etc., and can be applied to at least a portion of the set of walls of the first chamber 20 using any solution.

As described herein, the set of ultraviolet radiation sources 26B in the second chamber 30 can emit ultraviolet radiation 28B in the UV-C range. In an embodiment, the set of ultraviolet radiation sources 26B can operate in the range of approximately 260 nm to approximately 290 nm. This wavelength range can effectively destroy any microorganisms within the water and eliminate the presence of bacteria to a target level. Similar to the first chamber 20, in an embodiment, one or more interior surfaces of the second chamber 30 can include reflective regions. In a more specific embodiment, the reflective regions can be specular or diffusively reflective. In an embodiment, such a reflective region of the reflective surface can comprise polished aluminum or a reflective fluoropolymer, such as EFEP, expanding polytetrafluoroethylene ePTFE membrane (e.g., GORE® DRP® Diffuse Reflector Material), PTFE (e.g., Teflon®), and/or the like. The second chamber 30 can be configured to contain the radiation within the chamber so that the UV-C radiation does not exit the chamber.

Similar to the first chamber 20, in an embodiment, at least a portion of the set of walls for the second chamber 30 can also include a photocatalyst. In an embodiment, the set of ultraviolet radiation sources 26B that emit UV-C radiation 28B can be combined with a photocatalyst located on at least a portion of the set of walls of the second chamber 30 to improve disinfection. The photocatalyst can comprise any suitable photocatalyst, such as for example, $TiO_2$, copper, silver, copper/silver particles, platinum/palladium particles, etc., and can be applied to at least a portion of the set of walls of the second chamber 30 using any solution.

As also described herein, the third chamber 40 can also include a set of ultraviolet radiation sources 26C that emit UV-C ultraviolet radiation 28C. In an embodiment, the set of ultraviolet radiation sources 26C can operate in the range of approximately 260 nm to approximately 290 nm. In an embodiment, the interior surfaces of the third chamber 40 can include a set of reflective regions and/or a photocatalyst, similar to the first and second chambers 20, 30.

In an embodiment, the system 1 can comprise a control unit 50 (e.g., a microcontroller), which is configured to control operation of the components within the enclosure 10 (e.g., the set of ultraviolet radiation sources 26A-26C, the humidifier component 24, and/or the like). Such a control unit 50 can include logic for implementing a more complicated operation regime, e.g., determining a suitable intensity, duration, pattern, location, and/or the like, of the ultraviolet radiation, and operating the set of ultraviolet radiation source(s) 26A-26C according to the determined operation regime. In an embodiment, the control unit 50 can operate each set of ultraviolet radiation sources, 26A-26C, the humidifier component 24, and/or other components of the enclosure 10 separately. For example, the control unit 50 can turn on one of the sets of ultraviolet radiation sources 26A-26C without turning on the humidifier component 24 to create water vapor. In another example, the control unit 50 can turn on one or more of the sets of ultraviolet radiation sources 26A-26C, while the remaining sets of ultraviolet radiation sources 24A-26C are turned off and/or the humidifier component 24 is turned off.

The system 1 can include a feedback component 70 that is configured to acquire data used to monitor a set of current conditions for the enclosure 10 over a period of time. As illustrated, the feedback component 70 can include a plurality of sensing devices 72, each of which can acquire data used by the control unit 50 to monitor the set of current conditions. In an embodiment, the set of current conditions can include an amount of water within each chamber 20, 30, a residency time of water within each chamber 20, 30, whether the enclosure 10 is turned on/off, a level of fluorescence from each of the chambers 20, 30, 40, a humidity level for the vapor within the third chamber 40, a transparency of the water within each chamber 20, 30, a presence of microorganisms within each chamber 20, 30, 40, a change in visible properties (e.g., color of the water, mold, and/or the like) within each chamber 20, 30, 40, and/or the like.

The feedback component 70 can include one or more additional devices. For example, the feedback component 70 is shown including a logic unit 74. In an embodiment, the logic unit 70 receives data from a set of sensing devices 72 and provides data corresponding to the set of current conditions for the enclosure 10 for processing by the control unit 50. For example, the logic unit 70 can adjust the operation of one or more of the sensing devices 72, operate a unique subset of the sensing devices 72, and/or the like. In response to data received from the feedback component 70, the control unit 50 can automatically adjust and control one or more aspects of the ultraviolet radiation generated by the set(s) of ultraviolet radiation sources 26A-26C, such as the intensity, wavelength, duration, pattern, direction, location, and/or the like.

In an embodiment, the set of sensing devices 72 can include a fluorescent sensor, a visible sensor (e.g., a camera), a humidity sensor, a chemical sensor, and/or the like. In an embodiment, each of the chambers 20, 30, 40 can include any number of sensors. For example, the first chamber 20 can include a set of sensors that are used to determine the transparency of the water to UV-A radiation. In operation, the control unit 50 can receive this data from the feedback component 70 and automatically adjust and control the ultraviolet radiation 28A generated by the set of ultraviolet radiation sources 26A within the first chamber 20. In an embodiment, the second chamber 30 can include sensors similar to those located in the first chamber 20. In an embodiment, the third chamber 40 can include any type of sensors included in the first and second chambers 20, 30, including a humidity sensor to determine a level of humidity within the third chamber 40. In an embodiment, a chemical sensor can be included in each chamber to analyze the water to determine the set of current conditions.

In an embodiment, the enclosure 10 can include a heating element and a fan located in any area along the fluid flow path 12. The fan can be located adjacent to the heating element in order to blow dry air over any of the components within the enclosure 10 under the condition of the absence of water. The treatment of dry air can prevent or reduce the proliferation of bacteria and microorganisms within the enclosure 10. The control unit 50 can operate the heating element and fan for a predetermined period of time after the enclosure 10 is turned off.

In any of the embodiments discussed herein, the system 1 can include a user interface 80 that allows the control unit 50 to send notifications to a user. For example, the control unit 50 via the user interface 80 can inform a user if the enclosure 10 requires cleaning. The user can be notified as to which chamber and/or component of the enclosure 10 requires cleaning. In an embodiment, each part of the enclosure 10 is manufactured in a way as to allow easy cleaning by hand. For example, a user with average sized hands can be able to reach all internal walls of each chamber. In an embodiment, the user interface 80 can allow the user to select one or several operating configurations for the enclosure, such as the production of water vapor, disinfecting one or more of the water within the chambers, air drying one or more of the chambers, and/or the like.

While the various devices are shown and described as being separate from the enclosure 10, it is understood that one or more components can be mounted to or within the enclosure 10. For example, the control unit 50 and/or the power source 60, could be mounted within the enclosure 10. In an embodiment, the control unit 50 and the power source 60 would be sufficiently protected from the fluid flow path 12 to avoid any water damage. Additionally, all or some of the feedback component 70 could be mounted within the enclosure 10. For example, each chamber 20, 30, 40, could include a set of sensors mounted within each chamber 20, 30, 40 using any means.

Figure 3:
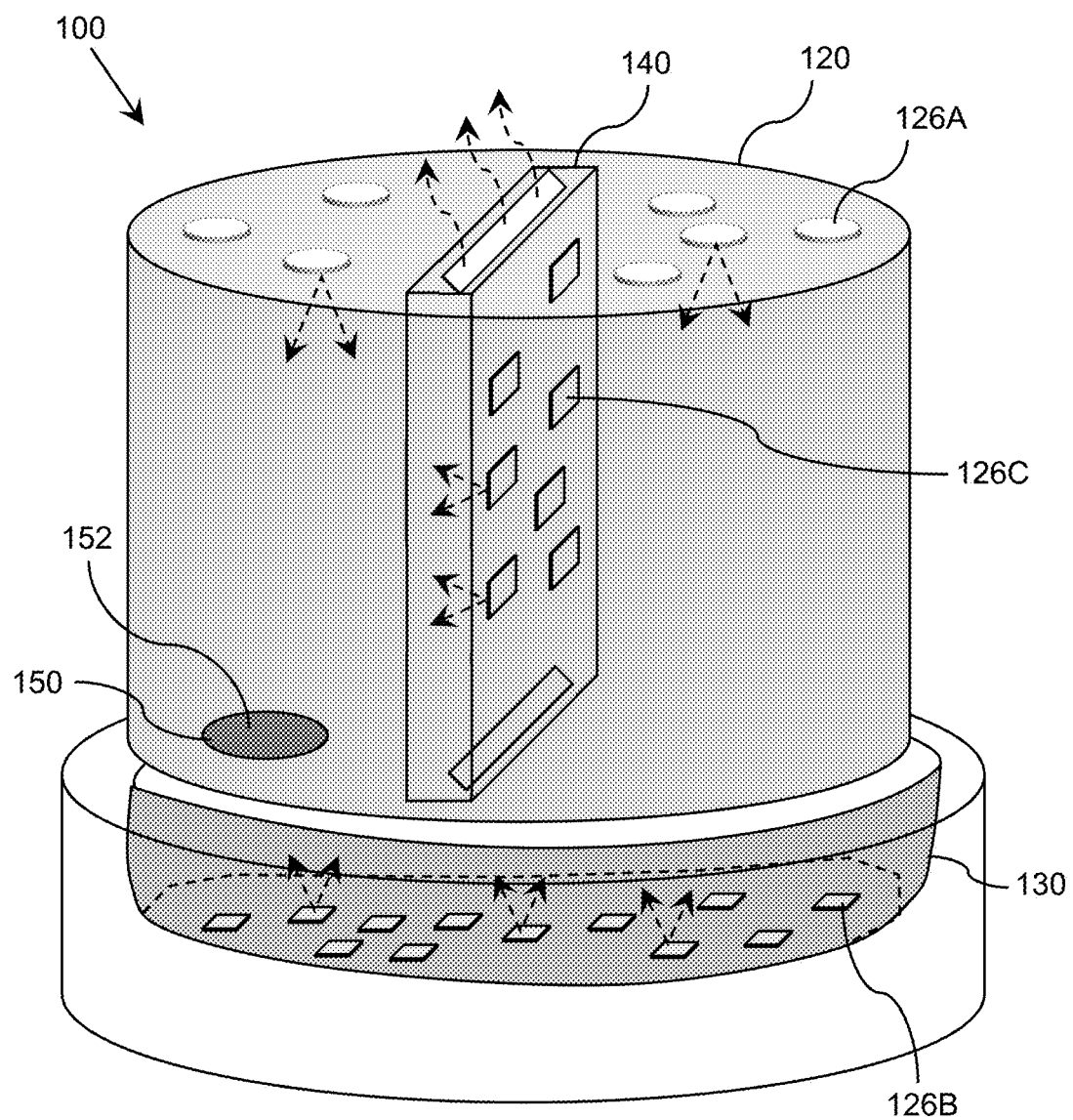
FIG. 3 shows an illustrative enclosure according to an embodiment.

Turning now to FIG. 3, an illustrative enclosure 100 according to an embodiment is shown. The enclosure 100 includes a first chamber 120, a second chamber 130, and a third chamber 140. As described herein, the first chamber 120, and the second chamber 130 are fluidly connected, e.g., via an opening 150, so that a small portion of the water located within the first chamber 120 flows into the second chamber 130. In an embodiment, a water filter 152 can be located between the first chamber 120 and the second chamber 130, e.g., within the opening 150. The first chamber 120 includes a set of ultraviolet radiation sources 126A that can operate in the UV-A wavelength range, while the second chamber 130 includes a set of ultraviolet radiation sources 126B that can operate in the UV-C wavelength range. In an embodiment, the set of ultraviolet radiation sources 126B are oriented to irradiate most, if not all, of the water located within the second chamber 130. For example, the set of ultraviolet radiation sources 126B within the second chamber are oriented to irradiate at least all of the water closest to a humidifier component 24 (FIG. 2) so that the water being evaporated into vapor for the third chamber 140 is sufficiently disinfected.

In this embodiment, the third chamber 140 is fluidly connected to the second chamber 130 and is located within the first chamber 120. The third chamber 140 includes a set of ultraviolet radiation sources 126C that can operate in the UV-C wavelength range. However, it is understood that this is only one example of the configuration of the enclosure 100 and that each chamber 120, 130, 140 can be any shape and size and are subject to the design of the enclosure 100.

Figure 4:
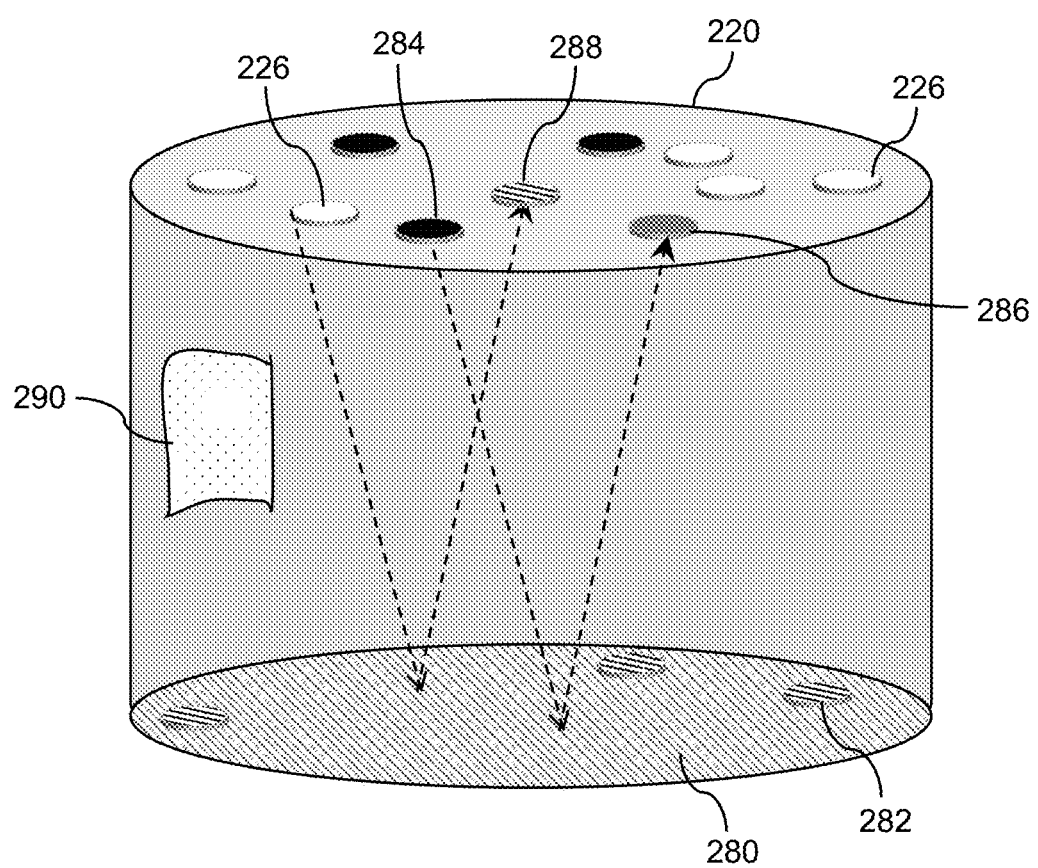
FIG. 4 shows an illustrative first chamber for an enclosure according to an embodiment.

Turning now to FIG. 4, an illustrative first chamber 220 according to an embodiment is shown. Although the first chamber 220 is shown as a cylinder, it is understood that the first chamber 220 can be any shape. As discussed herein, the first chamber 220 includes a set of ultraviolet radiation sources 226 that can operate in the UV-A wavelength range. In the figure, the set of ultraviolet radiation sources 226 are only located on the top surface of the first chamber 220, but it is understood that the set of ultraviolet radiation sources 226 can be located on any surface. However, a surface opposite the set of ultraviolet radiation sources 226 (in this case, the bottom surface of the first chamber 220) can include a reflective region 280, as discussed herein, to recycle the ultraviolet radiation within the first chamber 220. The first chamber 220 can also include a set of UV-A radiation sensors 282 that determine the transparency of the water to UV-A radiation, which can be used to increase or decrease a level of the UV-A radiation being emitted by the ultraviolet radiation sources 226.

As discussed herein, in an embodiment, the first chamber 220 can also include a set of fluorescent sources 284 configured to generate an ultraviolet radiation wavelength that induces a fluorescent signal from one or more contaminants that may be present within the water. The fluorescent signal can be measured by a set of fluorescent sensors 286. In an embodiment, the first chamber 220 can include a set of visible sensors (e.g., a camera) to capture images of the first chamber 220 in order to determine changes in the set of current conditions. In an embodiment, the camera is configured to detect biofouling within the chambers. It is understood that one or more other surfaces of the first chamber 220 can be configured to assist in disinfecting the water. For example, as illustrated by region 290, the interior side surface(s) of the first chamber 220 can include a photocatalyst.

Although only the first chamber 220 is shown in FIG. 4, it is understood that the features described herein in conjunction with the first chamber 220 can also be included in the second chamber 130 and the third chamber 140 (FIG. 3). It is understood that the second chamber 130 and the third chamber 140 can include photocatalysts, fluorescent sensors, visible sensors, reflective regions, and/or the like. For example, the second chamber 130 and/or the third chamber 140 can include a set of ultraviolet radiation sensors that determine the transparency of the water to UV-C radiation.

Figure 5A:
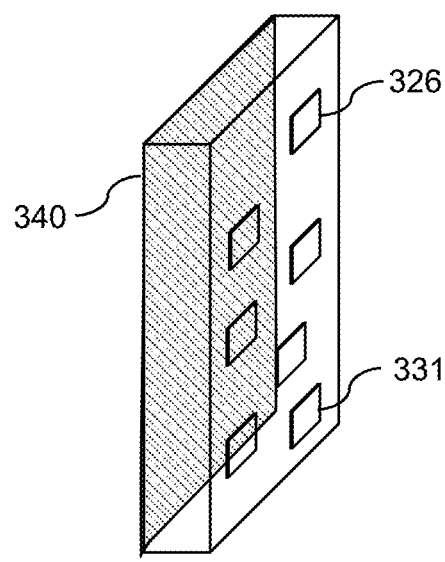
FIGS. 5A and 5B show illustrative third chambers for an enclosure according to an embodiment.
Figure 5B:
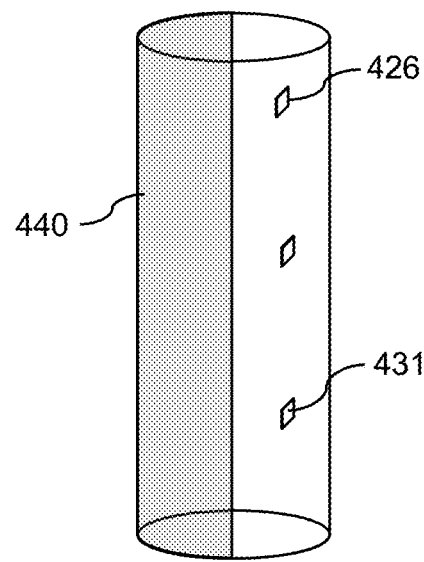

Turning now to FIGS. 5A and 5B, illustrative third chambers 340, 440 according to embodiments are shown. As illustrated, the third chamber 340, 440 can include a set of ultraviolet radiation sources 326, 426 that operate in the UV-C wavelength range. The ultraviolet radiation generated by the set of ultraviolet radiation sources 326, 426 can further improve disinfection of the vapor. A surface located opposite the ultraviolet radiation sources 326, 426 can be configured to improve mixing of the ultraviolet radiation (e.g., be reflective) or be configured to prevent ultraviolet radiation from leaving the chamber (e.g., be absorbing). The third chamber 340, 440 can also include a humidity sensor 331, 431 configured to measure the humidity level within the third chamber 340, 440.

In any of the embodiments discussed herein, the humidifier component 24 (FIG. 2) can include a fan that is blown over a wick to create water vapor (e.g., an evaporative humidifier). In an embodiment, a set of ultraviolet radiation sources can be located adjacent to the wick in order to generate ultraviolet radiation (UV-C wavelength) towards the wick. The UV-C radiation can prohibit proliferation of microorganisms within the wick. In an embodiment, the wick within the humidifier component 24 is easily replaceable.

As used herein, unless otherwise noted, the term "set" means one or more (i.e., at least one) and the phrase "any solution" means any now known or later developed solution. The singular forms "a," "an," and "the" include the plural forms as well, unless the context clearly indicates otherwise. Additionally, the terms "comprises," "includes," "has," and related forms of each, when used in this specification, specify the presence of stated features, but do not preclude the presence or addition of one or more other features and/or groups thereof.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. An enclosure comprising:
   a first chamber containing a volume of water, the first chamber including a first set of ultraviolet radiation sources configured to generate ultraviolet radiation in a UV-A wavelength range;
   a second chamber fluidly connected to the first chamber, the second chamber including a second set of ultraviolet radiation sources configured to generate ultraviolet radiation in a UV-C wavelength range, wherein a portion of the volume of water flows into the second chamber;
   a humidifier component adjacent to the second chamber configured to create water vapor from the portion of the volume of water within the second chamber;
   a third chamber connected to the humidifier component, the third chamber configured to contain the water vapor and release the water vapor into ambient; and
   a control unit configured to monitor a set of current conditions for the first chamber and the second chamber and adjust operation of the first set of ultraviolet radiation sources and the second set of ultraviolet radiation sources based on the set of current conditions.

2. The enclosure of claim 1, wherein at least one of: the first chamber or the second chamber includes a reflective region located on an interior surface configured to recycle the ultraviolet radiation within the chamber.

3. The enclosure of claim 2, wherein the reflective region is formed of a fluoropolymer.

4. The enclosure of claim 2, wherein the first chamber includes the reflective region and wherein the first set of ultraviolet radiation sources are positioned to direct ultraviolet radiation towards the reflective region.

5. The enclosure of claim 1, further comprising a set of sensors, wherein at least one sensor is configured to measure the transparency of the volume of water to UV-A and UV-C radiation, and wherein the set of current conditions includes a transparency of the water to UV-A and UV-C radiation.

6. The enclosure of claim 1, further comprising a visual camera configured to detect the set of current conditions of at least one of: the first chamber or the second chamber, wherein the set of current conditions includes a visual appearance of biofouling within at least one of: the first chamber or the second chamber.

7. The enclosure of claim 1, wherein the control unit monitors a set of current conditions for the third chamber, wherein the set of current conditions for the third chamber includes a humidity level for the water vapor.

8. The enclosure of claim 7, wherein the third chamber includes a third set of ultraviolet radiation sources configured to operate in the UV-C wavelength range.

9. The enclosure of claim 1, wherein the volume of water is stored in the first chamber for a period of time that is longer than a period of time the portion of the volume of water is stored in the second chamber.

10. A system comprising:
    a humidifier comprising:
    a first chamber containing a volume of water, the first chamber including a first set of ultraviolet radiation sources configured to generate ultraviolet radiation in a UV-A wavelength range;
    a second chamber fluidly connected to the first chamber, the second chamber including a second set of ultraviolet radiation sources configured to generate ultraviolet radiation in a UV-C wavelength range, wherein a portion of the volume of water flows into the second chamber;
    a humidifier component adjacent to the second chamber configured to create water vapor from the portion of the volume of water within the second chamber; and
    a third chamber connected to the humidifier component, the third chamber configured to contain the water vapor and release the water vapor into ambient; and
    a control unit configured to monitor a set of current conditions for the first chamber and the second chamber, the set of current conditions including a transparency of the water to UV-A and UV-C radiation, and adjust operation of the first set of ultraviolet radiation sources and the second set of ultraviolet radiation sources based on the set of current conditions.

11. The system of claim 10, wherein at least one of: the first chamber or the second chamber includes a reflective region located on an interior surface configured to recycle the ultraviolet radiation within the chamber.

12. The enclosure of claim 11, wherein the first chamber includes the reflective region and the first set of ultraviolet radiation sources are positioned to direct ultraviolet radiation towards the reflective region.

13. The system of claim 10, further comprising a set of sensors, wherein at least one sensor is configured to measure the transparency of the volume of water to UV-A and UV-C radiation.

14. The system of claim 13, wherein the set of sensors includes a visual camera configured to detect the set of current conditions of the first chamber and the second chamber, wherein the set of current conditions further includes a visual appearance of biofouling within the first chamber or the second chamber.

15. The system of claim 10, wherein the control unit monitors a set of current conditions for the third chamber, wherein the set of current conditions for the third chamber includes a humidity level for the water vapor.

16. The system of claim 15, wherein the third chamber includes a third set of ultraviolet radiation sources configured to operate in the UV-C wavelength range.

17. The system of claim 10, wherein the volume of water is stored in the first chamber for a period of time that is longer than a period of time the portion of the volume of water is stored in the second chamber.

18. A system comprising:
a humidifier comprising:
a first chamber containing a volume of water, the first chamber including a first set of ultraviolet radiation sources configured to generate ultraviolet radiation in a UV-A wavelength range;
a second chamber fluidly connected to the first chamber, the second chamber including a second set of ultraviolet radiation sources configured to generate ultraviolet radiation in a UV-C wavelength range, wherein a portion of the volume of water flows into the second chamber;
a humidifier component adjacent to the second chamber configured to create water vapor from the portion of the volume of water within the second chamber; and
a third chamber connected to the humidifier component, the third chamber including a third set of ultraviolet radiation sources configured to generate ultraviolet radiation in the UV-C wavelength range, wherein the third chamber is configured to contain the water vapor and release the water vapor into ambient; and
a control unit configured to monitor a set of current conditions for the first chamber, the second chamber, and the third chamber, the set of current conditions including a humidity level within the third chamber, and adjust operation of the first set of ultraviolet radiation sources, the second set of ultraviolet radiation sources, and the third set of ultraviolet radiation sources based on the set of current conditions.

19. The system of claim 18, wherein the humidifier further comprises a set of sensors configured to measure the set of current conditions.

20. The system of claim 19, wherein the set of sensors includes at least one sensor configured to measure the transparency of the volume of water to UV-A and UV-C radiation, wherein the set of current conditions further includes a transparency of the water to UV-A and UV-C radiation.

* * * * *